United States Patent
VanTassel et al.

(10) Patent No.: US 6,605,061 B2
(45) Date of Patent: Aug. 12, 2003

(54) CATHETER FOR DRUG INJECTION IN CARDIOVASCULAR SYSTEM

(75) Inventors: Robert A. VanTassel, Excelsior, MN (US); Robert S. Schwartz, Rochester, MN (US); David R. Holmes, Rochester, MN (US)

(73) Assignee: Tricardia, L.L.C., Excelsior, MN (US)

( * ) Notice: Subject to any disclaimer, the term of this patent is extended or adjusted under 35 U.S.C. 154(b) by 0 days.

(21) Appl. No.: 09/880,575

(22) Filed: Jun. 13, 2001

(65) Prior Publication Data

US 2001/0049500 A1 Dec. 6, 2001

Related U.S. Application Data

(63) Continuation of application No. 09/353,512, filed on Jul. 14, 1999, now abandoned.

(51) Int. Cl.[7] .............................................. A61M 5/178
(52) U.S. Cl. .............................. 604/164.01; 604/96.01; 604/264; 604/532
(58) Field of Search ............................ 604/19, 22, 48, 604/507–510, 93.01, 95.01, 506, 95.03, 95.04, 96.01, 104, 105, 106, 115, 116, 131, 156, 164.01, 164.12, 165.01, 181, 187, 218, 239, 240, 264, 272, 523, 530, 531, 532; 606/167, 159, 185

(56) References Cited

U.S. PATENT DOCUMENTS

| | | | | |
|---|---|---|---|---|
| 4,578,061 A | * | 3/1986 | Lemelson | 604/164 |
| 5,354,279 A | * | 10/1994 | Hofling | 604/164 |
| 5,360,416 A | * | 11/1994 | Ausherman et al. | 604/272 |
| 5,464,395 A | * | 11/1995 | Faxon et al. | 604/96 |
| 5,538,504 A | * | 7/1996 | Linden et al. | 604/53 |
| 6,053,900 A | * | 4/2000 | Brown et al. | 604/500 |

* cited by examiner

*Primary Examiner*—Brian L. Casler
*Assistant Examiner*—Jennifer Maynard
(74) *Attorney, Agent, or Firm*—Nikolai & Mersereau, P.A.

(57) ABSTRACT

A catheter for injecting medicants into the endocardium, myocardium or other portions of the cardiovascular system is presented where the catheter has apertures therein for ejection and retraction of a needle. The catheter is designed for the apertures in the catheter to press against the tissue to be injected in the heart while the heart is beating. A needle for inserting a prescribed dose of a medicant is ejected through the aperture and a plunger, pump, or diaphragm is moved to deliver a dose of the medicant to tissue adjacent the aperture. By use of the catheter gene therapy, wherein a small does of a gene are injected into the endocardium of the right or left ventricle, can be used to grow new blood vessels in the injected area of a damaged heart. The apertures in the catheter can be spaced at a prescribed distance for the dosage of medicant to form a precise pattern of injections in the area to be treated. The catheters may be used for any treatments of a human or animal patient where injections are required in the heart, veins or arteries of the cardiovascular system.

30 Claims, 4 Drawing Sheets

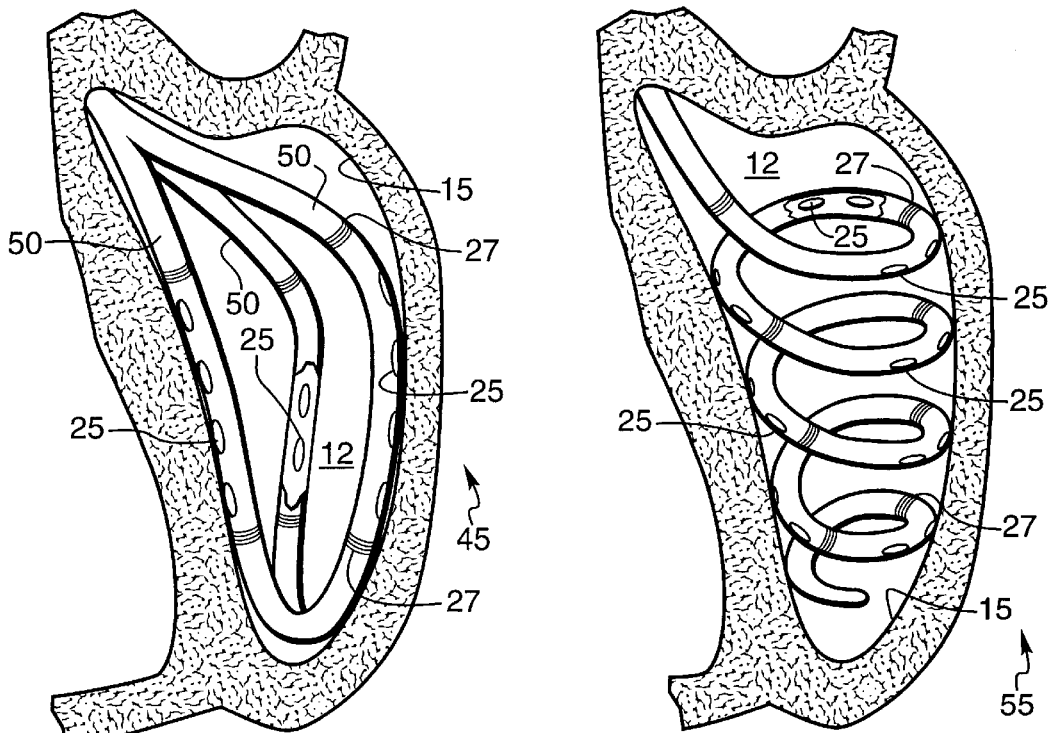
*Fig. 5*
*Fig. 6*
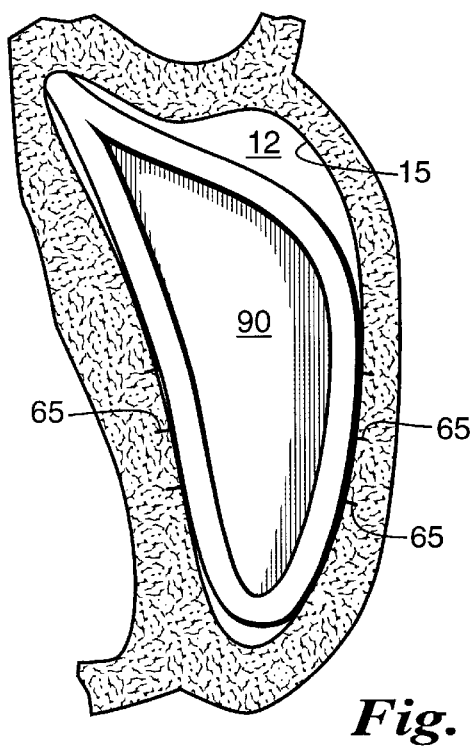
*Fig. 7*

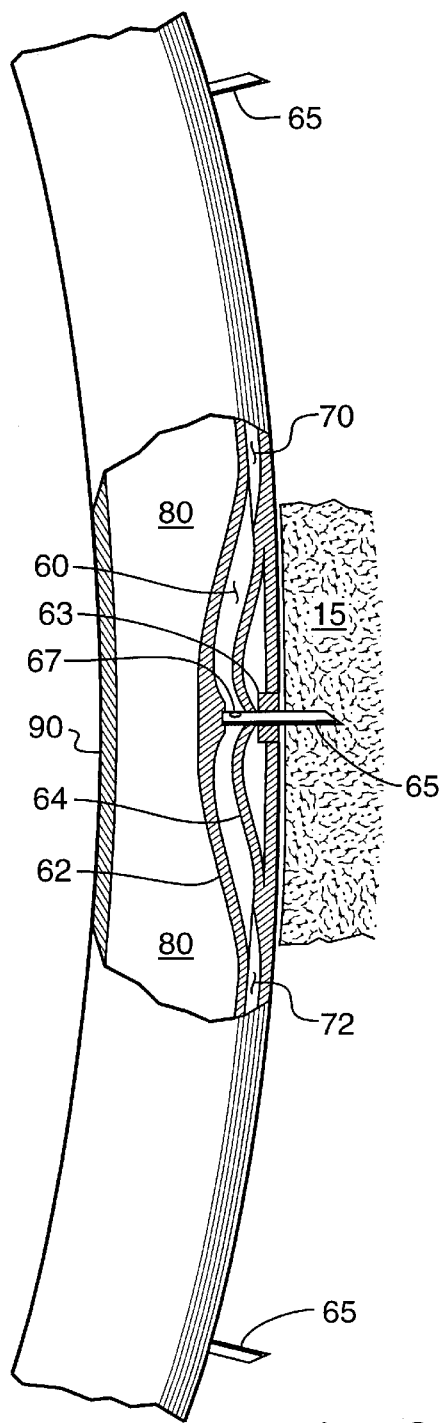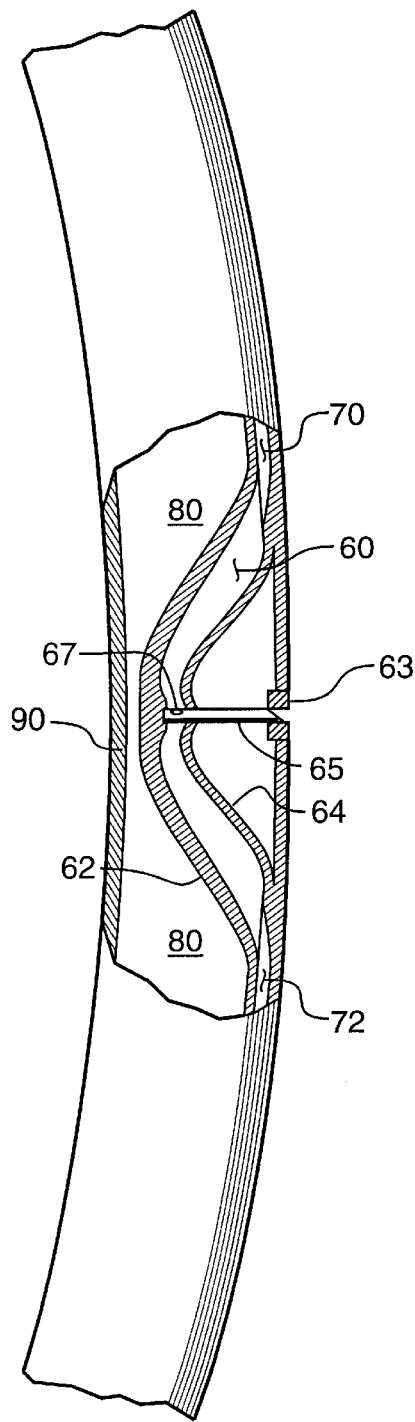
*Fig. 8*   *Fig. 9*

CATHETER FOR DRUG INJECTION IN CARDIOVASCULAR SYSTEM

This application is a continuation of Application Ser. No. 09/353,512 filed Jul. 14, 1999, now abandoned.

BACKGROUND OF THE INVENTION

1. Field of the Invention

This invention relates to catheters and more particularly to a catheter for injecting an agent at specified positions of the heart muscle (myocardium).

2. Description of Related Art

In the past devices have been used for minimally invasive techniques to access the heart, veins and arteries immediately adjacent by inserting catheters into the larger veins and arteries of the neck, arm and leg. These devices are used for balloon angioplasty, laser surgery, to make endoscopic observations of valves, plaque buildup and other cardiac conditions, or to take pressure and temperature readings in various chambers of the heart and in the nearby veins and arteries. Even microsurgery can be performed by these minimally invasive techniques. Dyes, radioactive materials, radiopaque contrast materials or other substances can be added to the heart by such devices to aid in x-rays, CAT scans or other observations and measurements of the heart. However there is no currently available means for accurate patterned delivery of gene injection therapies or other injections into the myocardium of the various chambers of the heart or into the veins and arteries nearby.

SUMMARY OF THE INVENTION

The invention is for minimally invasive delivery of agents for the treatment of medical conditions in the heart or adjacent veins and arteries where precision injection of genes or other agents is required in the treatment of the patient.

A catheter is inserted into the patient's veins or arteries of the arm, leg, or neck and threaded to the heart or other area to be injected with a medicant.

The catheter firmly presses against the tissue to be injected. The pressure of the catheter against the tissue to be treated may be by a fluid pressure in the catheter, by wires in the catheter or by a catheter with a material shaping to a memory position. The catheter has at least one aperture for a needle to be inserted therethrough or withdrawn therefrom to inject a medicant into tissue adjacent the apertures of the catheter. The needle can be on the end of a stylet which is mechanically sprung to eject from an aperture when the needle point is aligned with an aperture of the catheter. A plunger may be depressed to push a medicant of a known dose into the tissue adjacent the aperture or a pump may be used to inject the medicant. Alternatively a needle can be forced through an aperture by fluid pressure within the catheter acting on a mechanism to insert the needle into the tissue to be injected. The same fluid pressure may be used to pump a known amount of a medicant through the needle, or as above a plunger or a pump may be used.

OBJECTS OF THE INVENTION

It is an object of the invention to minimally invasively inject agents into or through the endocardium or myocardium.

It is an object of the invention to provide a precision pattern of injections in the endocardium or myocardium.

It is an object of the invention to provide gene therapy or introduce other therapeutic agents to the heart.

It is an object of the invention to provide a catheter for injecting a medicant into or through the interior walls of the cardiovascular system such as veins, arteries and chambers of the heart.

Other objects, advantages and novel features of the present invention will become apparent from the following detailed description of the invention when considered in conjunction with the accompanying drawing.

BRIEF DESCRIPTION OF THE DRAWINGS

FIG. 5 is a sectional view of the left ventricle with a cage catheter therein.

FIG. 6 is a sectional view of the left ventricle with a spiral catheter therein.

FIG. 7 is a sectional view of the left ventricle with a multiple needle catheter therein.

FIG. 8 is a sectional view of a multiple needle catheter with the needle extended.

FIG. 9 is a sectional view a multiple needle catheter with the needle withdrawn.

DESCRIPTION OF THE PREFERRED EMBODIMENTS

The invention presented herein shows the treatment of the left ventricle in the figures and described in the various embodiments of the specification, but it should be understood that any chamber of the heart or nearby veins and arteries may be treated with the device herein presented and variations thereof.

Figure 1:
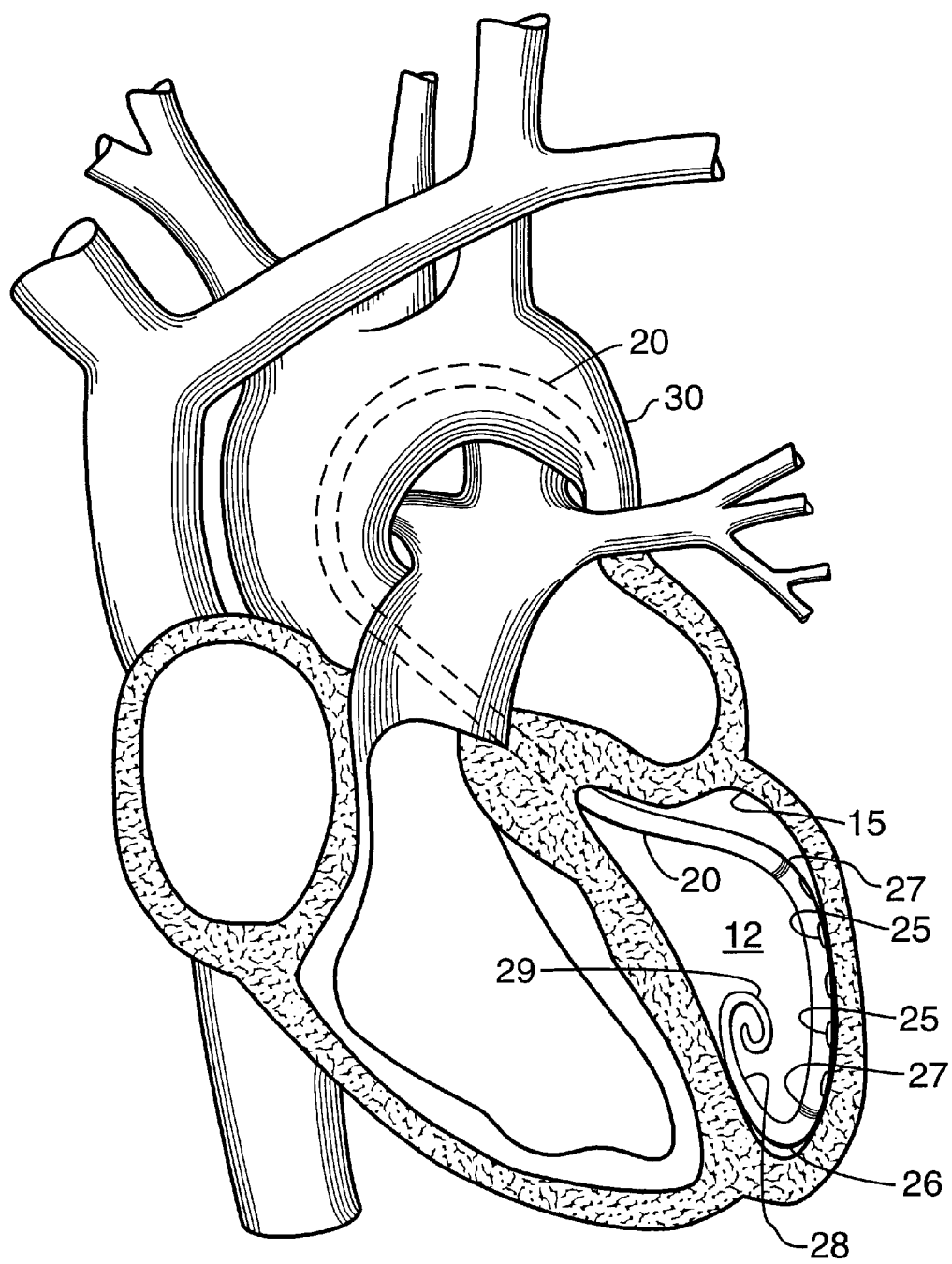
FIG. 1 is a perspective of a heart with the catheter inserted into the left ventricle.

FIG. 1 shows a perspective sectional view of a human heart 10 with a catheter 20 inserted therein. It should be understood that although the body of the specification refers to and shows a human heart 10, any animal having a similar cardiovascular system may be treated by the devices shown herein or modifications thereof, to fit the animal treated. The catheter 20 in the embodiment of FIG. 1 is routed retrograde though the aorta 30 and semilunar valve to the left ventricle 12.

Figure 2:
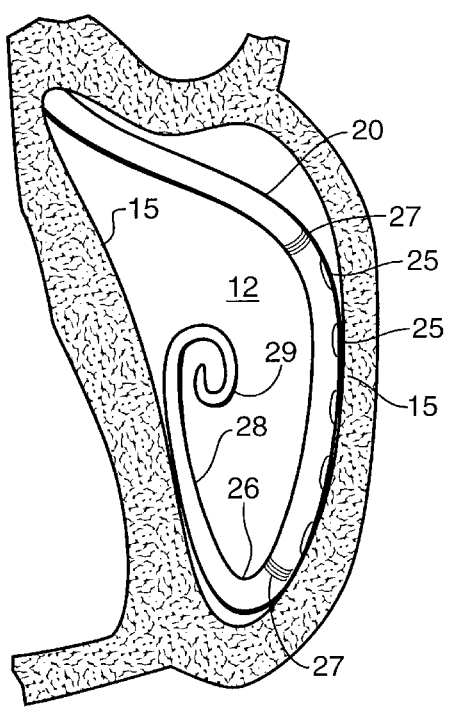
FIG. 2 is a sectional view of the left ventricle with a pigtail catheter inserted.

The catheter 20 in the first embodiment shown in FIGS. 1 and 2 is a pigtail catheter wherein the catheter 20 has a pigtail 29 at the distal end which is useful for routing the catheter through the aorta 30 and into the left ventricle 12. The pigtail 29 presents a curved end which will not exit an artery wall or damage heart tissue as it is inserted into the patient.

As best seen in FIG. 2 catheter 20 is lodged firmly against the endocardium 15 of the left ventricle 12 by the shape of the catheter 20 having a wall portion 28 which in conjunction with the curved base portion 26 acts like a spring for urging the catheter portion with the apertures 25 toward a section of the left ventricle endocardium 15 to be injected with a substance such as a drug, gene or other agents used in a prescribed treatment of a patient. Since the heart will be beating while the catheter 20 is in place the catheter 20 must be made of a flexible and compliant material capable of bending with the beating of the heart such that the apertures 25 will remain adjacent the endocardium 15 when the heart beats. To accomplish this, the apertures 25 are preferably on a curved section of catheter 20 which will nominally match the contours of the wall of the left ventricle to be treated. The catheter 20 may be a balloon type, as in FIG. 4, which is inflated once inside of the left ventricle, with the pressure in the balloon portion 80 holding the catheter to the desired shape. The balloon portion inflation lumen 80 can be filled with a fluid to give the catheter 20 a shape. Balloon wall 85 is attached to one side of the catheter 20 or alternatively made integral with the catheter. In other embodiments the stiffening of the catheter for holding its shape may be by stiffening wires 100 or springs in the catheter. For example in FIG. 4 the inflation lumen 80 could be used to insert a wire for providing a stiff backing for catheter 20. Alternatively a memory material can be used which is held straight by a stiffening stylet which when removed allows the catheter to take a desired shape.

The catheter 20 has apertures 25 for allowing a needle 65 or stylet 40 to exit the catheter and access a portion of the endocardium or myocardium 15 for injection of a substance for treating the patient. In the embodiment shown in FIGS. 3 and 4 the stylet 40 has an arched section 43 which is in arched contact with one wall of the catheter 20 such that its distal tip 44 is urged against the opposing wall of the catheter 20. When the distal tip 44 is on the catheter wall opposite the apertures 25 it may be inserted into or withdrawn from the catheter without emerging from the apertures 25. When the distal tip 44 is rotated to a position as in FIG. 4 the distal tip 44 will be aligned with the apertures 25. The compression of the arched portion 43 will force the distal tip 44 to emerge from the apertures 25 of the catheter 20 enough to puncture the endocaridial tissue 15 to a predetermined depth for injection of a substance, when the stylet 40 is drawn up the catheter 20. Since the distal tip 44 is angled downward away from the arched portion 43, then as the stylet 40 is drawn further up the catheter 20 the distal tip 44 will be pulled out of the tissue and through the aperture 25 into the catheter 20 and the force of the distal tip 44 on the wall of the catheter 20 will force the arched portion 43 against the opposite wall of the catheter 20 thus spring loading the distal tip 44 for ejection at the next aperture 25. The process is repeated at all the injection points for the treatment. The distal tip 44 of the stylet 40 therefore functions as a needle for injecting a substance for treating a patient.

A grove 95 in the wall of catheter 20 will help align the stylet 40 inside of the catheter 20 when either the arch section 43 or the distal tip 44 of the stylet 40 rides in the groove 95.

The apertures 25 may be spaced apart at different intervals for different treatments. As an example, for a therapeutic substance, the apertures may be on the order of 10 mm from center to center. The stylet 40 would be on the order of a gauge 25–27. The catheter 20 has markers 27 at the top and bottom of the range of apertures 25 such that the catheter 20 is viewable as to its position in the patient. For example the markers may be magnetic and a magnetic sensor would be used to find the position of the marker. Alternatively if the marker 27 is used in a CAT scan, x-ray or flouroscopy it may be a more or less opaque material than the rest of the catheter 20, for example a band of gold may be used as the opaque material.

The groove 95 may extend the length of the catheter 20 or just the length of the section of the catheter 20 having apertures 25 since that is the portion where the distal tip 44 needs to be properly aligned.

Figure 4:
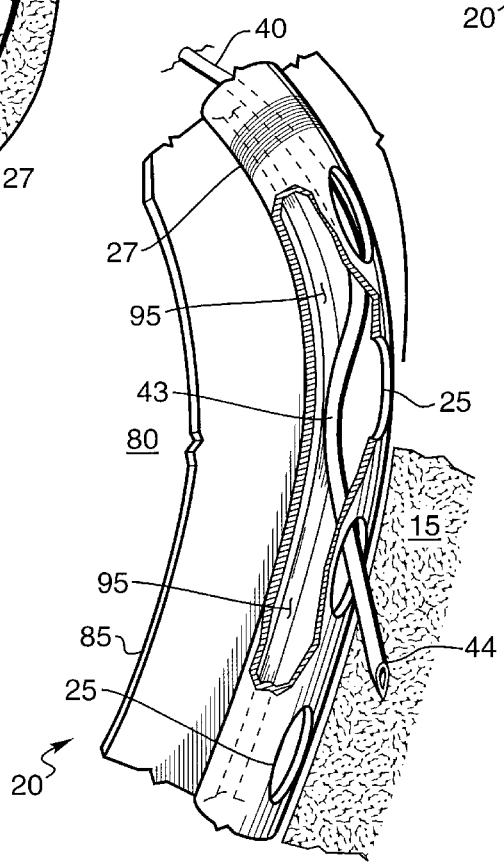
FIG. 4 is a sectional view of the catheter and the stylet therein with the needle pointing toward the apertures.

In FIG. 5 a second embodiment is shown as a cage catheter 45. In the embodiment shown the cage has three struts 50 for forming the cage but any number of struts 50 may be used. For example if two struts 50 are used the cage catheter 45 would form a loop in the left ventricle 12. In the embodiment shown in FIG. 5 with three struts 50, the cage catheter 45 performs the function of forming an outer wall pressed against the endocardium 15 in the left ventricle 12 such that the apertures 25 are firmly held in place while the heart 10 is beating. The cage catheter 45 may be a balloon type with a structure as shown in FIG. 4. The struts 50 of the cage catheter 45 are forced outward against the endocardium such as by fluid pressure injected into the cage catheter 45 after it is inserted into the left ventricle 12. In this manner the heart may continue pumping since the volume of the left ventricle 12 is largely unobstructed. The cage catheter 45 has the advantage of being able to more securely place the apertures 25 next to the endocardium 15 since all the struts 50 are mutually forcing the apertures 25 to the endocardium 15.

In the cage catheter 45 embodiment the stylet 40 operates as before, but now has three paths to follow such that the patient can receive more injection points for the treatment or optionally only one strut 50 would have apertures 25 for treating only a small portion of the endocardium 15. The markers 27 will be used as before to align apertures 25 for the treatment points.

If the two strut cage catheter 45 is used the stylet 40 can travel around the entire loop with apertures 25 being used serially rather than withdraw the stylet 40 and select a second strut 50.

In a third embodiment a spiral catheter 55 is used. The spiral catheter 55 may also be of the balloon type, as in FIG. 4, for inflation once it is inserted in the left ventricle 12. The spiral shape has the advantage of a single serial draw on the stylet 40 without having to select different struts 50 of the catheter as in the cage catheter 45 embodiment and the circular nature of the spiral catheter 55 can be used to apply pressure to the circumference of the spiral catheter to press the apertures 25 against the endocardium 15. Depending on the pitch of the spiral, a large number of injection points around the left ventricle 12 may be selected for treatment. As before the markers 27 can be used to align the apertures 25 with the area to be treated.

Figure 3:
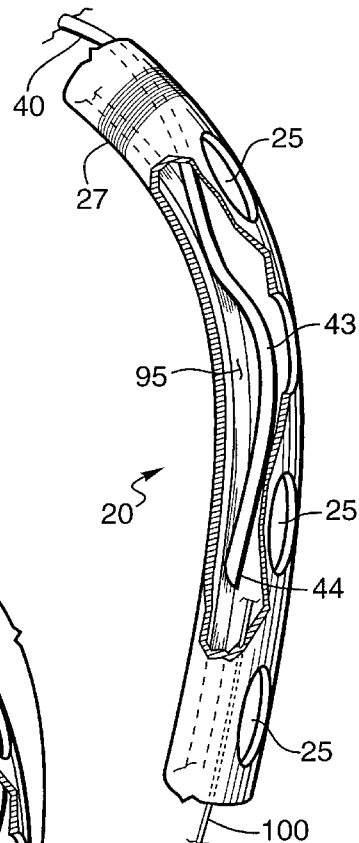
FIG. 3 is a sectional view of the catheter and the stylet therein with the needle pointing away from the apertures.

The stylet 40 in each of these embodiments may be preloaded in the catheter 20, the cage catheter 45, or the spiral catheter 55 or inserted in the catheters after they are in place in the left ventricle 12. The advantage of preloading is that the stylet 40 would not have to be turned to be aligned or unaligned with the apertures 25 on insertion and withdrawal. In an alternative embodiment a trough or groove 95 as shown in FIGS. 3, 4 may be used on the inside wall of the catheter 20, the cage catheter 45, or the spiral catheter 55 to align the stylet 40 by having either the arch 43 or distal tip 44 ride in the trough or groove 95 for only the portion of the catheter opposite the apertures 25.

The stylet 40 may have a lumen for transporting a medicant and a plunger, pump or other means of forcing the medicant out of the distal tip 44 when the distal tip 44 is injected into the tissue to be treated with the medicant.

In a fourth embodiment a multi-needle balloon catheter 90 is inserted into the left ventricle as shown in FIG. 7 and inflated. In the embodiment shown the multi-needle balloon catheter 90 has a two strut cage design but any number of struts may be used. The area treated is selected to be a small area with three needles used but any number of needles spaced close together of further apart can be used.

FIG. 8 shows a cross section of the multi-needle balloon catheter 90 which has a needle guard 63 for guiding the needle 65 out of the multi-needle balloon catheter 90 and limiting the stroke of needle 65. In the embodiment shown, when lumen 80 is filled with a fluid the needle 65 is moved outward from the catheter 90 by fluid pressure on wall 62. The medicant may be in a sack 60 formed by walls 62, 64 of the multi-needle balloon catheter 90. The medicant under pressure by wall 62 forces the medicant through apertures 67 in needle 65 for administering the medicant to the patient. Elastemetric wall 64 will be compressed during this stage and retract the needle 65 when pressure in lumen 80 is reduced. With the pressure in the catheter removed the needles 65 will be retracted, as in FIG. 9, and the multi-needle balloon catheter 90 can be safely withdrawn from the patient. In an alternate embodiment medicant 70 can be fed to needles 65 by means of tubes 70 connecting the needles 65 along the length of catheter 90. The medicant will then be injected after the needles 65 are pushed forward by fluid pressure in lumen 80.

The catheters 20, 45 and 55 and the stylet 40 may be moved into location and precisely placed adjacent areas of the cardiovascular system needing treatment by use of stepper motors for making a series of small movements on the catheters 20, 45, 55 to place the apertures 25 adjacent the areas to be injected. Stepper motors may also be used to precisely move the stylet 40 within the catheters to position the distal tip 44 at desired locations. Similarly stepper motors may be used in conjunction with a plunger in the stylet 40 to deliver precise amounts of medicant to the areas to be treated. Although stepper motors are mentioned above any type of motor or actuator which can be precisely controlled for the purposes described may be used with the invention.

The catheter 20, the cage catheter 45, and the spiral catheter 55 may all have stiffening stylets inside for holding the catheters straight while they are inserted into the patient. As the stylet is removed the catheter material assumes its material memory shape such as seen in the embodiments for a "I" shape catheter 20, cage catheter 45 or spiral catheter 55.

Obviously, many modifications and variations of the present invention are possible in light of the above teachings. It is therefore to be understood that, within the scope of the appended claims, the invention may be practiced otherwise than as specifically described. States is:

What is claimed is:

1. A cardiovascular injection catheter for injecting medicants into tissues of the cardiovascular system comprising:
   a needle for injecting a medicant into tissue,
   a catheter having at least one radial aperture through the catheter wall for ejection and withdrawal of the needle therethrough,
   the catheter has a spiral shape having a diameter approximating the size of a chamber of the cardiovascular system to be injected, such that the at least one radial aperture of the spiral shaped catheter abuts the tissue to be injected,
   a means for ejecting and retracting the needle through the at least one aperture in the catheter such that the needle can inject a specified dose of medicant into the tissue at specific locations.

2. A cardiovascular injection catheter as in claim 1 wherein:
   the needle comprises a stylet having a distal tip and an arched portion for spring loading the distal tip for ejecting the distal tip into the tissue when the distal tip is aligned with one of the at least one aperture.

3. A cardiovascular injection catheter as in claim 2 wherein:
   the catheter contains a groove for engaging and guiding the stylet such that the distal tip of the stylet is aligned in a known position relative to the apertures.

4. A cardiovascular injection catheter as in claim 2 wherein:
   the stylet has a lumen with a medicant therein for injecting a specified volume of medicant into the tissue.

5. A cardiovascular injection catheter as in claim 1 wherein:
   the needle is attached to a pressure activated movable wall which ejects the needle from the catheter into the tissue when fluid pressure is applied to the wall and withdraws the needle from the tissue when fluid pressure is removed from the wall.

6. A cardiovascular injection catheter as in claim 5 wherein:
   a medicant is enclosed in a sac formed by the wall of the catheter and the movable wall, the medicant injected through the needle as the wall provides pressure to force the medicant through the needle.

7. A cardiovascular injection catheter as in claim 5 wherein:
   a tube for medicant fluidly connected to the needle for injecting a specified volume of medicant into the tissue.

8. A cardiovascular injection catheter as in claim 1 wherein:
   a balloon portion on the catheter provides shape and stiffness to the catheter.

9. A cardiovascular injection catheter as in claim 1 wherein:
   a wire portion on the catheter provides shape and stiffness to the catheter.

10. A cardiovascular injection catheter as in claim 1 wherein:
    markers on the catheter placed adjacent the at least one radial aperture in the catheter allow for placement of the at least one radial aperture adjacent the tissues in the cardiovascular system to be injected with medicant.

11. A cardiovascular injection catheter for injecting medicants into tissues of the cardiovascular system comprising:
    a needle for injecting a medicant into tissue,
    catheter having at least one radial aperture through the catheter wall for ejection and withdrawal of the needle therethrough,
    the catheter having struts forming a cage catheter, wherein the struts approximate the volume a chamber of the cardiovascular system to be injected, the struts having apertures abutting the tissue to be injected,
    a means for ejecting and retracting the needle through the at least one aperture in the catheter such that the needle can inject a specified dose of medicant into the tissue at specific locations.

12. A cardiovascular injection catheter as in claim 11 wherein:
    the needle comprises a stylet having a distal tip and an arched portion for spring loading the distal tip for ejecting the distal tip into the tissue when the distal tip is aligned with one of the at least one aperture.

13. A cardiovascular injection catheter as in claim 12 wherein:
    the catheter contains a groove for engaging and guiding the stylet such that the distal tip of the stylet is aligned in a known position relative to the apertures.

14. A cardiovascular injection catheter as in claim 12 wherein:

the stylet has a lumen with a medicant therein for supplying medicant injected into the tissue.

15. A cardiovascular injection catheter as in claim 11 wherein:

the catheter contains a needle attached to a pressure activated movable wall which ejects the needle from the catheter into the tissue when fluid pressure is applied to the wall and withdraws the needle from the tissue when fluid pressure is removed from the wall.

16. A cardiovascular injection catheter as in claim 15 wherein:

a medicant is enclosed in a sac formed by the wall of the catheter and the movable wall, the medicant injected through the needle as the wall provides pressure to force the medicant through the needle.

17. A cardiovascular injection catheter as in claim 15 wherein:

a tube for medicant fluidly connected to the needle for supplying medicant injected into the tissue.

18. A cardiovascular injection catheter as in claim 11 wherein:

a balloon portion on the catheter provides shape and stiffness to the catheter.

19. A cardiovascular injection catheter as in claim 11 wherein:

a wire portion on the catheter provides shape and stiffness to the catheter.

20. A cardiovascular injection catheter as in claim 11 wherein:

markers on the catheter placed adjacent the at least one radial aperture in the catheter allow for placement of the at least one radial aperture adjacent the tissues in the cardiovascular system to be injected with medicant.

21. A cardiovascular injection catheter for injecting medicants into tissues of the cardiovascular system comprising:

a needle for injecting a medicant into tissue, a tubular catheter having at least one radial aperture through the catheter wall for ejection and withdrawal of the needle therethrough, the catheter has two portions connected by a curved base portion which forces the two portions apart such that the at least one aperture in at least one of the two portions of the catheter abut the tissue to be injected, a means for ejecting and retracting the needle through the at least one aperture in the catheter such that the needle can inject a specified dose of medicant into the tissue at specific locations.

22. A cardiovascular injection catheter as in claim 21 wherein:

the needle comprises a stylet having a distal tip and an arched portion for spring loading the distal tip for ejecting the distal tip into the tissue when the distal tip is aligned with one of the at least one aperture.

23. A cardiovascular injection catheter as in claim 22 wherein:

the catheter contains a groove for engaging and guiding the stylet such that the distal tip of the stylet is aligned in a known position relative to the apertures.

24. A cardiovascular injection catheter as in claim 21 wherein:

the needle is attached to a pressure activated movable wall which ejects the needle from the catheter into the tissue when fluid pressure is applied to the wall and withdraws the needle from the tissue when fluid pressure is removed from the wall.

25. A cardiovascular injection catheter as in claim 22 wherein:

the stylet ha s a lumen with a medicant therein for supplying medicant injected into the tissue.

26. A cardiovascular injection catheter as in claim 24 wherein:

a medicant is enclosed in a sac formed by the wall of the catheter and the movable wall, the medicant injected through the needle as the wall provides pressure to force the medicant through the needle.

27. A cardiovascular injection catheter as in claim 24 wherein:

a tube for medicant fluidly connected to the needle supplying medicant for injection into the tissue.

28. A cardiovascular injection catheter as in claim 21 wherein:

a balloon portion on the catheter provides shape and stiffness to the catheter.

29. A cardiovascular injection catheter as in claim 21 wherein:

a wire portion on the catheter provides shape and stiffness to the catheter.

30. A cardiovascular injection catheter as in claim 21 wherein:

markers on the catheter placed adjacent the at least one radial aperture in the catheter allow for placement of the at least one radial aperture adjacent the tissues in the cardiovascular system to be injected with medicant.

* * * * *